(12) United States Patent
Fell

(10) Patent No.: US 8,974,372 B2
(45) Date of Patent: Mar. 10, 2015

(54) PATH-FOLLOWING ROBOT

(76) Inventor: Barry M. Fell, Hummelstown, PA (US)

( * ) Notice: Subject to any disclaimer, the term of this patent is extended or adjusted under 35 U.S.C. 154(b) by 282 days.

(21) Appl. No.: 13/218,318

(22) Filed: Aug. 25, 2011

(65) Prior Publication Data

US 2012/0221016 A1 Aug. 30, 2012

Related U.S. Application Data

(60) Provisional application No. 61/376,829, filed on Aug. 25, 2010.

(51) Int. Cl.
*A61B 1/00* (2006.01)
*A61B 19/00* (2006.01)

(52) U.S. Cl.
CPC ..... *A61B 19/2203* (2013.01); *A61B 2019/2238* (2013.01)
USPC ........... 600/114; 600/139; 600/141; 600/142; 600/152

(58) Field of Classification Search
USPC ......... 600/114, 141–152; 901/23; 318/568.11
See application file for complete search history.

(56) References Cited

U.S. PATENT DOCUMENTS

| | | | |
|---|---|---|---|
| 3,986,692 A | 10/1976 | Kinoshita | |
| 4,683,406 A * | 7/1987 | Ikeda et al. | 318/568.2 |
| 4,834,519 A | 5/1989 | Twisselmann | |
| 4,930,494 A * | 6/1990 | Takehana et al. | 600/145 |
| 5,251,611 A | 10/1993 | Zehel et al. | |
| 5,289,948 A | 3/1994 | Moss et al. | |
| 5,348,259 A | 9/1994 | Blanco et al. | |
| 5,482,029 A * | 1/1996 | Sekiguchi et al. | 600/109 |
| 5,609,565 A | 3/1997 | Nakamura | |
| 5,624,380 A * | 4/1997 | Takayama et al. | 600/146 |
| 5,662,587 A | 9/1997 | Grundfest et al. | |
| 5,916,147 A * | 6/1999 | Boury | 600/146 |
| 5,918,844 A | 7/1999 | Ognier | |
| 5,921,694 A | 7/1999 | Herbermann | |
| 6,238,124 B1 | 5/2001 | Merlo | |
| 6,379,073 B1 | 4/2002 | Yoo et al. | |
| 6,610,007 B2 * | 8/2003 | Tartaglia et al. | 600/146 |
| 6,672,788 B2 | 1/2004 | Hathaway | |
| 6,767,153 B1 | 7/2004 | Holbrook | |
| 6,790,173 B2 | 9/2004 | Saadat et al. | |
| 6,824,510 B2 * | 11/2004 | Kim et al. | 600/114 |
| 6,835,173 B2 | 12/2004 | Couvillon, Jr. | |
| 6,871,563 B2 * | 3/2005 | Choset et al. | 74/490.05 |
| 6,899,673 B2 | 5/2005 | Ogura et al. | |
| 7,090,637 B2 | 8/2006 | Danitz et al. | |
| 7,250,027 B2 | 7/2007 | Barry | |

(Continued)

OTHER PUBLICATIONS

Lee et al. "A Highly Redundant Robot System for Inspection", NASA Conference Publication. Mar. 21, 1994.*

*Primary Examiner* — Matthew J Kasztejna
(74) *Attorney, Agent, or Firm* — Brooks Kushman P.C.

(57) ABSTRACT

A path-following robot, such as for creating a path to a target surgical site, includes a series of interconnected elements including a lead element at one end thereof, and a plurality of actuators each operably coupled to one of the plurality of elements. Each actuator is capable of effecting rotational and spherical motion of one element with respect to another element. The actuators are arranged to receive commands which individually control the relative position of one element compared with another element, where a position of the lead element determines a path and corresponding positions for all subsequent elements to create a path-following motion.

19 Claims, 5 Drawing Sheets

(56) References Cited

U.S. PATENT DOCUMENTS

| | | | |
|---|---|---|---|
| 7,387,179 B2 * | 6/2008 | Anhalt et al. | 180/9.1 |
| 8,226,546 B2 * | 7/2012 | Belson | 600/114 |
| 8,317,777 B2 * | 11/2012 | Zubiate et al. | 606/1 |
| 8,328,714 B2 * | 12/2012 | Couvillon, Jr. | 600/146 |
| 8,361,090 B2 * | 1/2013 | Belson | 606/150 |
| 8,397,481 B2 * | 3/2013 | Zubiate et al. | 59/78.1 |
| 2002/0012566 A1 | 1/2002 | Auchinleck et al. | |
| 2002/0055668 A1 | 5/2002 | Pauker | |
| 2002/0091304 A1 | 7/2002 | Ogura et al. | |
| 2003/0032948 A1 | 2/2003 | Dubrowskij | |
| 2003/0036748 A1 | 2/2003 | Cooper et al. | |
| 2003/0083550 A1 | 5/2003 | Miyagi | |
| 2003/0149338 A1 | 8/2003 | Francois et al. | |
| 2005/0085693 A1 | 4/2005 | Belson et al. | |
| 2005/0137454 A1 | 6/2005 | Saadat et al. | |
| 2006/0058582 A1 | 3/2006 | Maahs et al. | |
| 2006/0111615 A1 | 5/2006 | Danitz et al. | |
| 2006/0173243 A1 | 8/2006 | Watanabe | |
| 2006/0178560 A1 | 8/2006 | Saadat et al. | |
| 2007/0027360 A1 | 2/2007 | Mitsuya | |
| 2007/0049800 A1 | 3/2007 | Boulais | |
| 2007/0135683 A1 | 6/2007 | Bob et al. | |
| 2007/0149852 A1 | 6/2007 | Noguchi et al. | |
| 2007/0232858 A1 | 10/2007 | Macnamara et al. | |
| 2007/0244360 A1 | 10/2007 | Ikeda | |
| 2007/0255104 A1 | 11/2007 | Maruyama | |
| 2007/0260115 A1 | 11/2007 | Brock et al. | |
| 2007/0282311 A1 | 12/2007 | Scott et al. | |
| 2008/0004606 A1 | 1/2008 | Swain et al. | |
| 2008/0039690 A1 | 2/2008 | Zubiate et al. | |

* cited by examiner

PATH-FOLLOWING ROBOT

CROSS-REFERENCE TO RELATED APPLICATIONS

This application claims the benefit of U.S. provisional Application No. 61/376,829 filed Aug. 25, 2010, the disclosure of which is incorporated in its entirety by reference herein.

TECHNICAL FIELD

Embodiments relate to a path-following robot, such as for use in endoscopy, laparoscopy, or other interventions.

BACKGROUND

Endoscopes are used in surgery to view internal portions of a patient's body, typically through a narrow incision in the body exterior. A typical flexible endoscope includes a long slender insertion section to be inserted into a body cavity of a patient, and an operation section coupled to a base end of the insertion section. The insertion section has a distal portion that incorporates an imaging unit. The endoscope also has one or more internal working channels through which a variety of instruments may be inserted.

The distal portion is attached to a bending portion that includes a plurality of annular joint elements connected in series, with adjacent joint elements pivotally joined together. Inside the joint pieces there are two pairs of operation wires: one for vertical turn and the other for horizontal turn. Pushing and pulling these operation wires leads the joint pieces to turn, and thereby the bending portion as a whole to bend in the vertical or horizontal direction. Endoscopes are typically only controlled in the XY orientation in the last 20 to 30 cm of length. The Z axis is controlled by linear movement of the endoscope from the operator. Pushing on a scope by the operator from the proximal end may not result in the desired linear motion of the distal tip due to looping or coiling of the scope along the way.

Existing endoscopes have a further shortcoming in that the endoscope needs a fulcrum to gain leverage to move tissue and properly apply tension and counter-tension with its accompanying tools. The location of where the fulcrum actually occurs along the length of the endoscope is highly variable and can lead to unpredictable motion or unsatisfactory control over the distal, working end of the endoscope and the associated instruments.

Other multiple element devices exist where each element is controlled via sets of wires or by pneumatic methods, electromechanical methods, length changing polymers, shape memory materials, or other generally linear methods of controlling the relative position of each element to the next element as well as the position of the lead element of the device. However, such existing devices utilize linear actuators and combinations of linear actuators and local locking mechanisms which limit the positioning capability to that of locking one element to the next in a fixed position.

DETAILED DESCRIPTION

Figure 1:
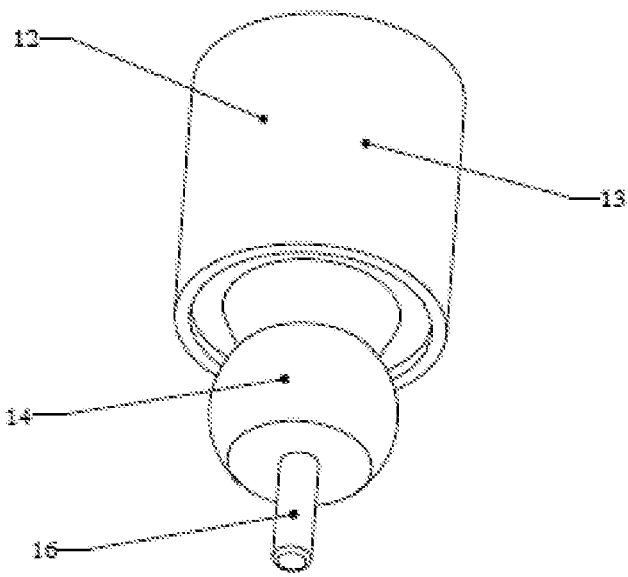
FIG. 1 is a perspective view of an element of an embodiment of a path-following robot.
Figure 2:
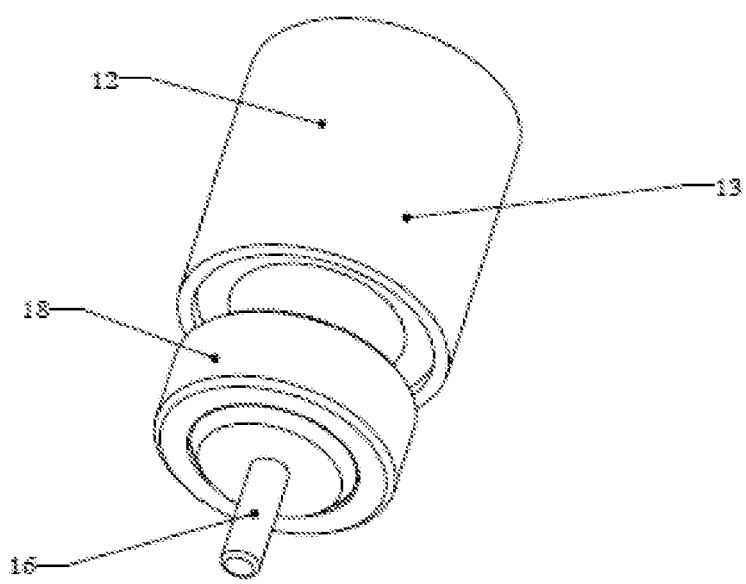
FIG. 2 is a perspective view of the element of FIG. 1 and a receiver for a spherical joint of the element.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Embodiments disclosed herein relate to a path-following robot comprising a series of interconnected elements, such as for use in endoscopic, laparoscopic, or other interventional procedures. By path-following, it is meant that each element in the robot has a location in space that is determined by the element preceding it on its course and, in turn, determines the course of the subsequent element or elements. For example, in accordance with the disclosed embodiments, in a robot comprising a series of twenty-six interconnected elements named A through Z, if at a particular moment in time element G is located at a specific set of coordinates in space, when the robot is advanced by the length of element G, the next element, H, will occupy the exact same spatial coordinates as element G.

With reference to FIGS. 1-6, in one embodiment, a motor-on-motor, spherical joint approach is utilized to provide a path-following robot, designated generally by reference numeral 10. Each element 12 in the robot 10 comprises an upper portion including a generally cylindrical, hollow housing 13 and a lower portion including a spherical joint 14 and a generally cylindrical positioning stem 16 extending therefrom. An annular receiver 18 is disposed within the housing 13 of each element 12 (shown separate from the housing 13 in FIG. 2 for ease of illustration) for receiving the spherical joint 14 of the subsequent element 12 in order to link the elements 12 together while allowing for relative movement.

Figure 6:
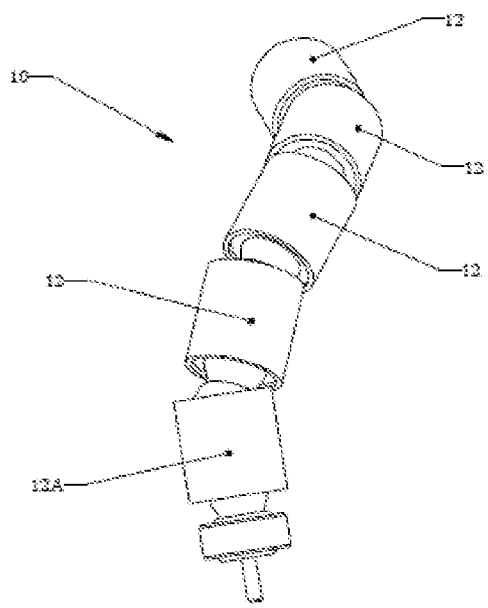
FIG. 6 is a perspective view of a path-following robot comprising a plurality of elements of FIG. 1, wherein the plane of each element is depicted.
Figure 10:
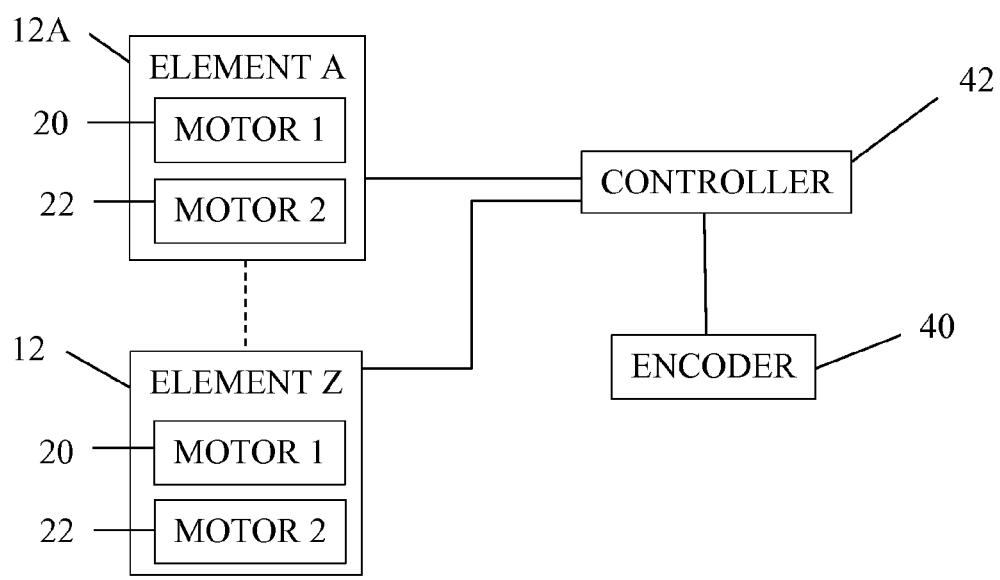
FIG. 10 is a block diagram schematically illustrated communication of the robot elements with a controller and encoder.

The lead element in the robot 10 can be named element A, shown as 12A in FIG. 6, and this element 12A is the element that is first inserted into an opening in a patient's body and determines the path that all subsequent elements 12 in the robot 10 will be forced to follow if a path-following motion is desired. The position of element 12A may be determined by means of a linear encoder 40 (FIG. 10) that determines the distance of travel of element 12A from the encoder "zero" position, in the typical case, at the point of entry into a patient's body. The zero position may be defined as a reference position on a fixed spatial position device that is co-located with some spatial reference to the patient. Embodiments of the path-following robot described herein are arranged to pass alongside or through such an encoder 40 and may use the encoder 40 as its reference point.

Figure 3:
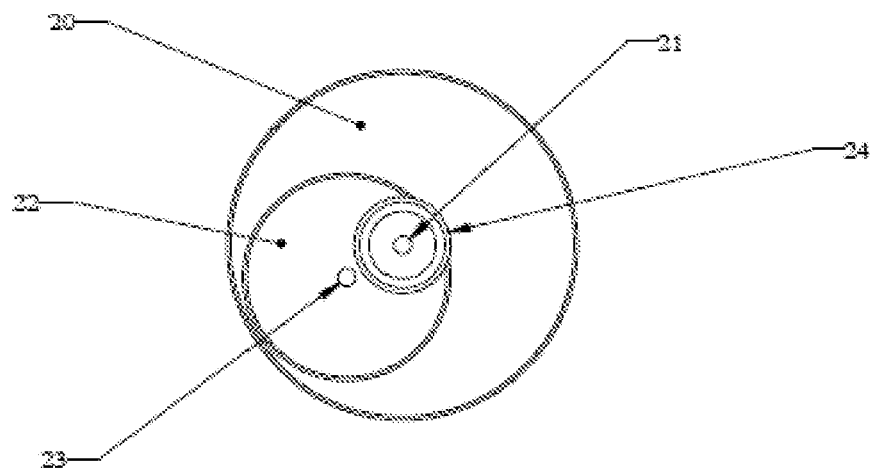
FIG. 3 is a top plan view of a concentric motor arrangement within each element of FIG. 1.

Also mounted within the housing 13 is a concentric, two-motor system as depicted in FIG. 3. The motor system includes a first, larger motor 20, capable of rotating with a center of rotation 21 relative to the element housing 13. Mounted to the first motor 20 is a second, smaller motor 22. In one embodiment, the second motor 22 has a center of rotation 23 located slightly less than one-half the radius of the second motor 22 away from the center of rotation 21 of the first motor 20. The second motor 22 includes a sleeve 24 for capturing the positioning stem 16 of the subsequent element 12 on the robot 10. Each motor 20, 22 may include an encoder, such as an optical encoder, such that the position of each motor 20, 22 in space relative to any reference (e.g., encoder 40 or another element 12) may be determined.

Figure 4:
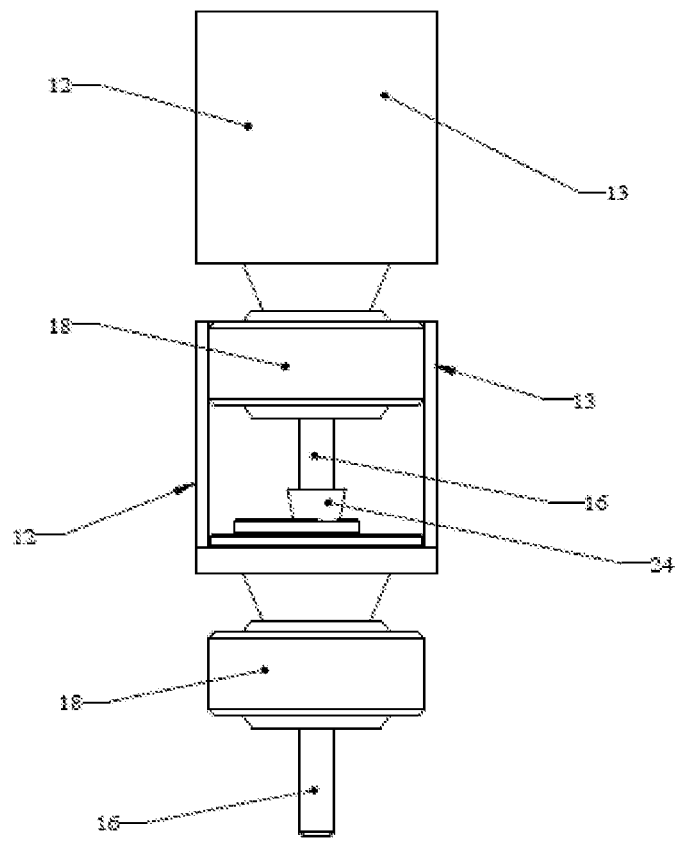
FIG. 4 is a side elevational, partially cut-away view of two adjacent elements of FIG. 1, wherein the lower element is cut-away to show engagement of a spherical joint of the upper element with the receiver of the lower element, and engagement of the positioning stem of the upper element within the motor sleeve of the lower element.
Figure 5:
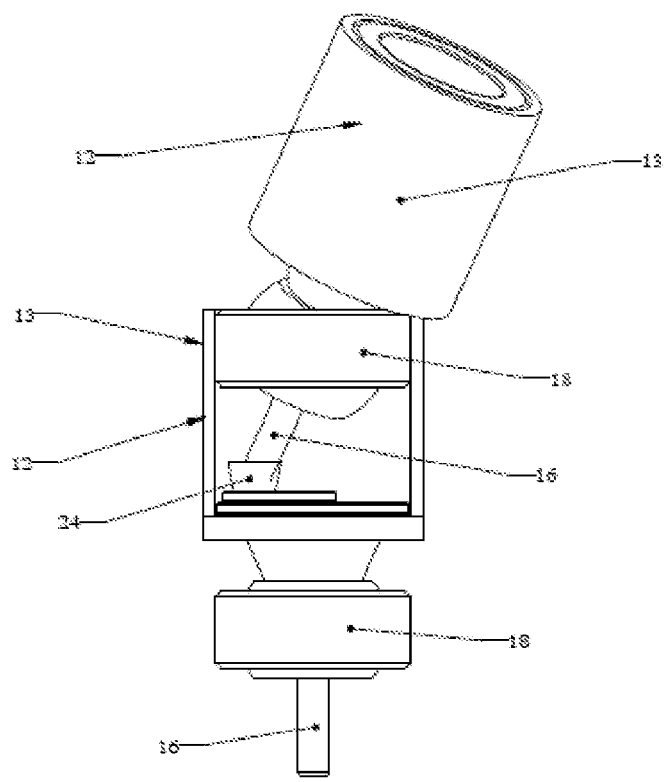
FIG. 5 is a side elevational, partially cut-away view of the adjacent elements of FIG. 4 illustrating tilt of the upper element due to the position of the motor sleeve of the lower element.

With reference to FIG. 4, if the second motor 22 is in a neutral position, the sleeve 24 is located above the center of rotation 21 of the first motor 20. In this manner, rotation of the first motor 20 will not cause angular displacement of the subsequent element 12, but can cause rotational motion if a splined sleeve 24 is utilized. With reference to FIG. 5, if the second motor 22 is rotated relative to the first motor 20, it results in a tilting of the immediately subsequent element 12.

If the position of each motor 20, 22 in a specific element 12 is known at all times, it is thus possible to determine the exact point in space of each element 12 in the robot 10 at all times, either relative to the position of the encoder 40 or another element 12. The linear travel of the robot 10 and the rotational and spherical positions of all of the elements 12 are known exactly because all of the elements 12 are mechanically linked through elements of known dimensions, and the relative spherical and rotational orientation of one element relative to the next along the robot 10 is also known. This also allows for determination of whether the elements 12 are in differing planes of orientation.

Further, via communication of each motor 20, 22 in each element 12 with a controller 42, it is possible to command the individual elements 12 in the robot 10 to follow a particular (e.g., serpentine) path by rotating the element motor combinations 20, 22 in the proper sequence and position. Communication between the controller 42 and the elements 12 may be accomplished by wired or wireless transmission including, but not limited to, RF and infrared methods. In one embodiment, the elements 12 will be able to achieve 360 degrees of rotation as well as spherical displacement of approximately +/−60 degrees, resulting in a generally cone-shaped area of possible element 12 location relative to the adjacent element 12. If a series of such elements 12 are linked together, differing paths of the robot 10, ranging from straight to complex, are possible. FIG. 6 depicts an exemplary multi-planar positioning of the elements 12 of the robot 10.

Therefore, each element 12 in the robot 10 includes encoded positional actuators (e.g., motors) that link the elements 12 together and allow for the tracking of the precise relational spherical (tilt) and rotational movement between any two elements 12. The relative position of element A may be recorded, relative to the next element B, for example, specifically as it relates to the rotational and spherical relationship between the two elements. When a chain of such elements is linked together, it is possible to know and control the exact spatial position of each element relative to its zero point and thus to each other. Specifically, if the spatial coordinate position of element A is known, then commands can be sent via a controller 42 (FIG. 10) to the individual element motors 20, 22, to effect the proper coordinate positioning of each element 12 in the robot 10 as each element 12 approaches its predetermined destination, as determined by lead element A as it passed through the desired point earlier in its travel.

Figure 7:
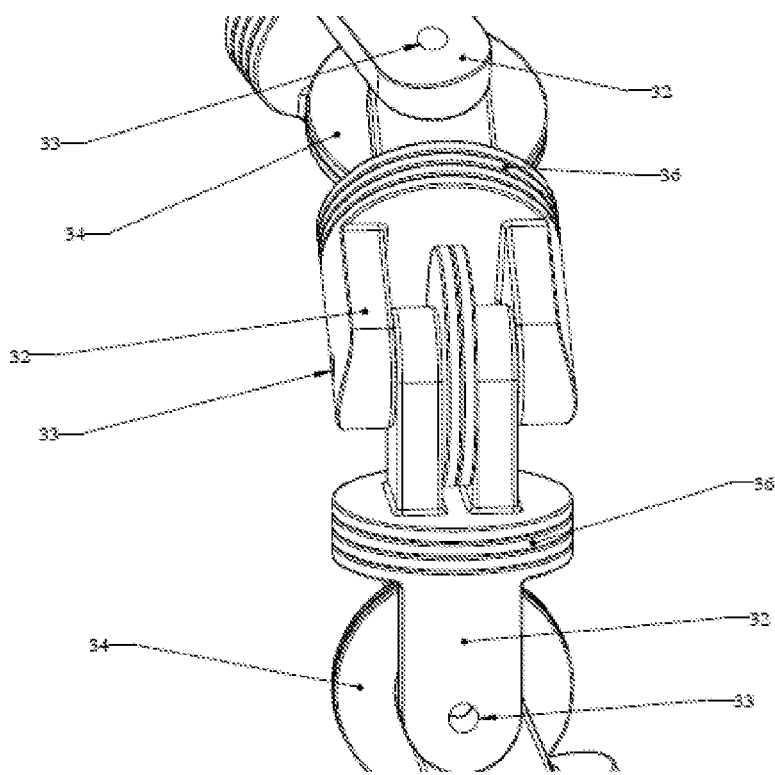
FIG. 7 is a perspective view of adjacent elements of another embodiment of a path-following robot.
Figure 8:
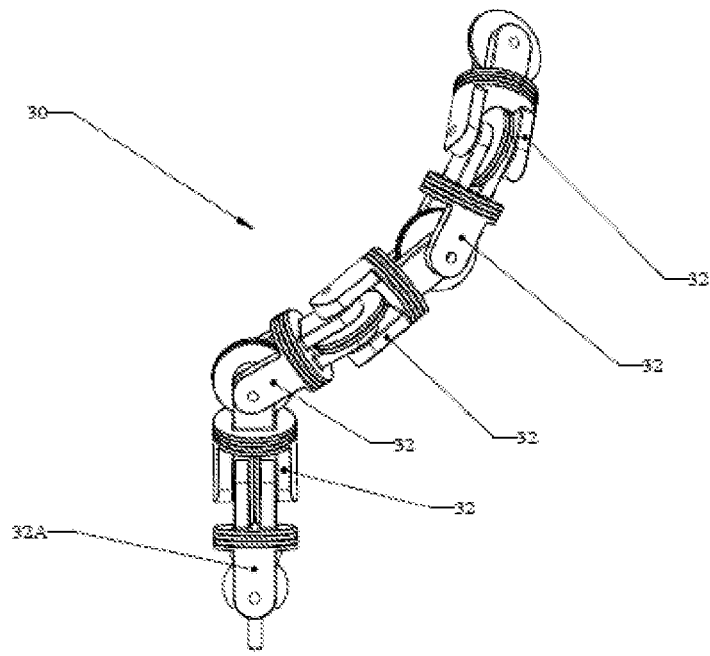
FIG. 8 is a perspective view of a path-following robot comprising a plurality of elements of FIG. 7, wherein the plane of each element is depicted.

With reference to FIGS. 7-8, in another embodiment, a robot utilizing a 90 degree opposing motor, double yoke element configuration is provided, designated generally by reference numeral 30. Each element 32 has a single plane, 180 degree of freedom arc of motion yoke joint 33 at each end, wherein the yoke joints 33 are offset by 90 degrees to one another. Each element 32 is joined together by a rotational motor 34 that has its axis of rotation located normal to the axis of robot travel. Optionally, the two yoke ends of any given adjacent elements 32 can be joined together via another motor 36 capable of 360 degrees of rotation and having its axis of rotation oriented parallel to the axis of travel of the robot 30. FIG. 8 depicts an exemplary multi-planar positioning of the elements 32 of the robot 30, wherein the lead element is designated as 32A. It is understood that features described above with reference to robot 10 may also be applicable to robot 30.

Therefore, embodiments of the robot 10, 30 disclosed herein are capable of individually controlling the relative position of one element to another via localized mechanical actuators which provide for relative motion of the elements, thus creating path-following capability. Of course, the robot embodiments described herein may also be used in procedures not requiring a path-following device. In addition, more than one robot at a time may be employed to perform a particular procedure. All elements in the robot 10, 30 may have the same dimensions, such as an equal length, but this is not a necessary requirement for path following to occur. The turn radius of the robot 10, 30 will be determined by the size of elements.

With the embodiments described herein, the robot 10, 30 is driven into the body through an externally applied force, such as drive wheels or human hands. Force applied may act to accelerate elements of the robot 10, 30 along the path created by the lead element, contrary to a traditional endoscope which may buckle and loop under such pressure. Once the robot 10, 30 is inside the body, and even once it is at its final target location, any individual element or set of elements can be moved, such as in order to create space or act as a retractor of tissue through its bulk.

The robot 10, 30 described herein is infinitely rotatable, which is advantageous when employed in an endoscopic or laparoscopic role. Not only can the lead element A rotate 360 degrees, but each subsequent element can do that as well. This rotational freedom allows for faster, more dexterous surgery. The combination of multiple spherically and rotationally capable elements is distinct from traditional endoscopes as well as newer inner/outer mechanisms, locking element mechanisms, and the rotating end effector of robotic surgery instruments (e.g., DA VINCI® surgical system).

Furthermore, elements of the robot 10, 30 disclosed herein can be selectively stiffened or their position locked through the use of the individual actuators (e.g., motors) used to control the relative motion of the elements. As a result, the robot 10, 30 has an almost limitless number of spatial configurations it can assume, and provides for the ability to customize and localize the surgical fulcrum. This is useful to the surgeon who desires more leverage of his instruments to be located closer to the target point of surgery. The typical endoscope is only capable of achieving this through the locking of the individual elements and the rigid laparoscope's fulcrum is determined by its entry point on the body.

Figure 9:
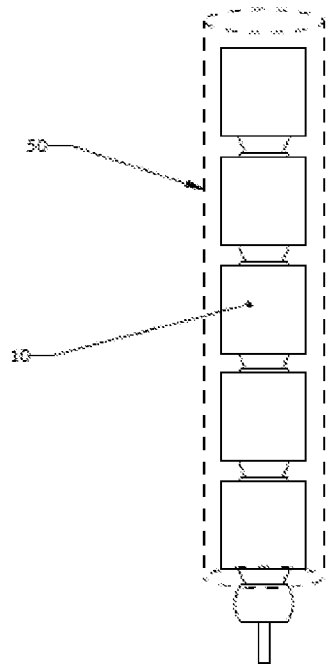
FIG. 9 is a perspective view of the path-following robot of FIG. 6 with an overtube introduced.

With reference to FIG. 9, the robot 10, 30 described herein can also be used in conjunction with a flexible or locking overtube 50 or the like to perform a surgical procedure. Once the robot 10, 30 has reached its target surgical destination, because it can be held in position along its entire length, it allows for the addition of an overtube 50 to be passed safely over the rigidified robot 10, 30. This differs from other prior methods of guided endoscopes, as they are subject to distortion and bending along their length as the overtube is introduced.

Once the robot 10, 30 is in the desired position, the overtube 50 can be slid over the outside of the robot 10, 30 into place along its entire length. Once the overtube 50 is in place, the robot 10, 30 can be allowed to go limp (i.e., releasing a locked position of each element with respect to adjacent elements) for safe removal and the overtube 50 used for the insertion of additional instrumentation. Alternatively, once the overtube 50 is in place, the robot 10, 30 can be replaced with a more traditional endoscope or flexible laparoscope. As such, the robot 10, 30 can be made with a very small diameter to allow for safe placement in the body, and then an overtube 50 subsequently used to facilitate entry of other instruments.

The robot 10, 30 may include an end effector, either at the lead element or possibly subsequent elements in close proximity, for performing functions at the target site. The end effector may include real-time image or navigational guidance, such as a fiber optic chip, to reach the target surgical site and potentially perform diagnostic imaging. Retractors, scissors, knives, suction, and other surgical tools can also be provided on board for additional functionality.

Therefore, the path-following robot 10, 30 described herein may function as a device to create a safe path from a first point (i.e., entry point on the body) to a second point (i.e., target surgical site). At the second point, the robot 10, 30 can perform functions or can create a guide for the insertion of an overtube 50.

The robot embodiments disclosed herein facilitate the use of surgical instruments such as retractors, scissors, knives, ablative instruments, suction, lavage and other surgical tools. The overtube 50 may have working channels along the perimeter thereof allowing the insertion of surgical instruments with the robot 10, 30 in place, or alternatively the robot 10, 30 may be removed and replaced with an endoscope, laparoscope, or other device. Since the robot 10, 30 can be adjustably rigidified along its length, the guide wires normally used with a traditional laparoscope or endoscope can still be used to effect instrument motion and function without causing harmful compression of the element joints which can cause a traditional laparoscope or endoscope to bind or affect the performance of the surgical instrument.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A path-following robot, comprising:
    a series of interconnected elements including a lead element at one end thereof, each element having an upper portion including a hollow housing; and
    a motor system mounted within an interior of the housing of each of the plurality of elements, the motor system including a first motor and a second motor mounted to the first motor in a stacked configuration, each motor system capable of effecting rotational and spherical motion of one element with respect to another element,
    wherein the motor systems are arranged to receive commands which individually control the relative position of one element compared with another element, wherein a position of the lead element determines a path and corresponding positions for all subsequent elements to create a path-following motion.

2. The robot according to claim 1, wherein the first and second motors each include an encoder for determining a position of the element.

3. The robot according to claim 1, wherein the second motor has a center of rotation located approximately one-half the radius of the second motor away from a center of rotation of the first motor.

4. The robot according to claim 1, wherein each element has a lower portion including a spherical joint and a positioning stem extending therefrom.

5. The robot according to claim 4, wherein the second motor includes a sleeve for receiving the positioning stem of a subsequent element.

6. The robot according to claim 1, further comprising a receiver disposed within the housing for receiving the spherical joint of a subsequent element.

7. The robot according to claim 6, wherein rotation of the second motor relative to the first motor in one element causes movement of the spherical joint of the subsequent element within the receiver, thus resulting in motion of the subsequent element.

8. The robot according to claim 1, wherein the lead element includes an end effector for performing functions at a target site.

9. The robot according to claim 1, wherein the elements are substantially equal in length.

10. A system for creating a path to a target surgical site within a body of a patient, the system comprising:
    a path-following robot comprising a series of interconnected elements including a lead element at one end thereof, each element having an upper portion including a hollow housing, and a motor system mounted within an interior of the housing of each of the plurality of elements, the motor system including a first motor and a second motor mounted to the first motor in a stacked configuration, each motor system capable of effecting rotational and spherical motion of one element with respect to another element; and
    a controller in communication with the motor systems to individually control the relative position of one element compared with another element, wherein a position of the lead element determines a path and corresponding positions for all subsequent elements to create a path-following motion.

11. The system according to claim 10, further comprising a reference encoder positioned at an opening of the body and in communication with the motor systems for determining a position of each element.

12. The system according to claim 10, wherein the first and second motors each include an encoder for determining a position of the element.

13. The system according to claim 10, wherein the second motor has a center of rotation located approximately one-half the radius of the second motor away from a center of rotation of the first motor.

14. The system according to claim 10, wherein each element has a lower portion including a spherical joint and a positioning stem extending therefrom.

15. The system according to claim 14, wherein the second motor includes a sleeve for receiving the positioning stem of a subsequent element.

16. The system according to claim 10, further comprising a receiver disposed within the housing for receiving the spherical joint of a subsequent element.

17. The system according to claim 16, wherein rotation of the second motor relative to the first motor in one element causes movement of the spherical joint of the subsequent element within the receiver, thus resulting in motion of the subsequent element.

18. The system according to claim 10, wherein the lead element includes an end effector for performing functions at a target site.

19. The system according to claim 10, wherein the elements are substantially equal in length.

* * * * *